United States Patent [19]

Topol

[11] 3,996,005
[45] Dec. 7, 1976

[54] DETECTION AND MEASUREMENT OF $NO_2$ AND $O_3$

[75] Inventor: Leo E. Topol, Canoga Park, Calif.

[73] Assignee: Rockwell International Corporation, El Segundo, Calif.

[22] Filed: Oct. 14, 1975

[21] Appl. No.: 622,300

[52] U.S. Cl. .................. 23/232 R; 23/232 E; 423/500; 423/504
[51] Int. Cl.² .................. C01B 7/00; G01N 21/26; G01N 27/26; G01N 33/00
[58] Field of Search ............ 23/232 R, 232 E; 423/500, 504

[56] References Cited
OTHER PUBLICATIONS

M. Dodé, Chem. Abstr. 32, 2861 (1938).
C. W. Wadelin, Anal. Chem. 29, 441 (1957).
Barr et al., J. Appl. Phys. 33, 225 (1962).

*Primary Examiner*—Robert M. Reese
*Attorney, Agent, or Firm*—L. Lee Humphries; Henry Kolin; Clark E. DeLarvin

[57] ABSTRACT

Small amounts of $NO_2$ and $O_3$ in air are determined by utilizing the reactions of these gases with solid alkali metal halides to produce halogen, and the reaction of $NO_2$ with various salts such as $PbI_2$ to produce NO; halogens produced from the reaction may be measured by the use of an electrolytic cell, the output of which is dependent on the halogen concentration of the gas contacting one electrode thereof, while the NO concentration may be determined by the chemiluminescence technique.

3 Claims, 3 Drawing Figures

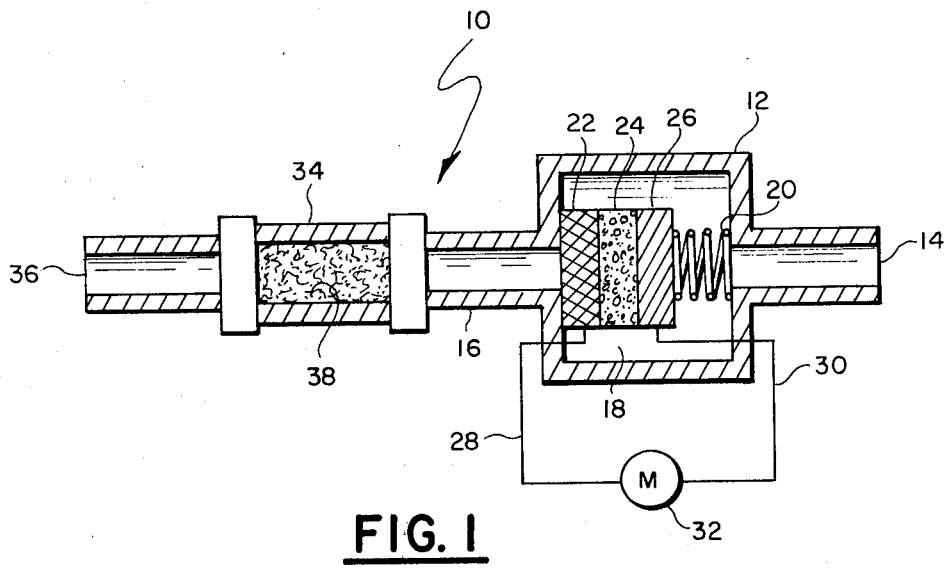
FIG. 1
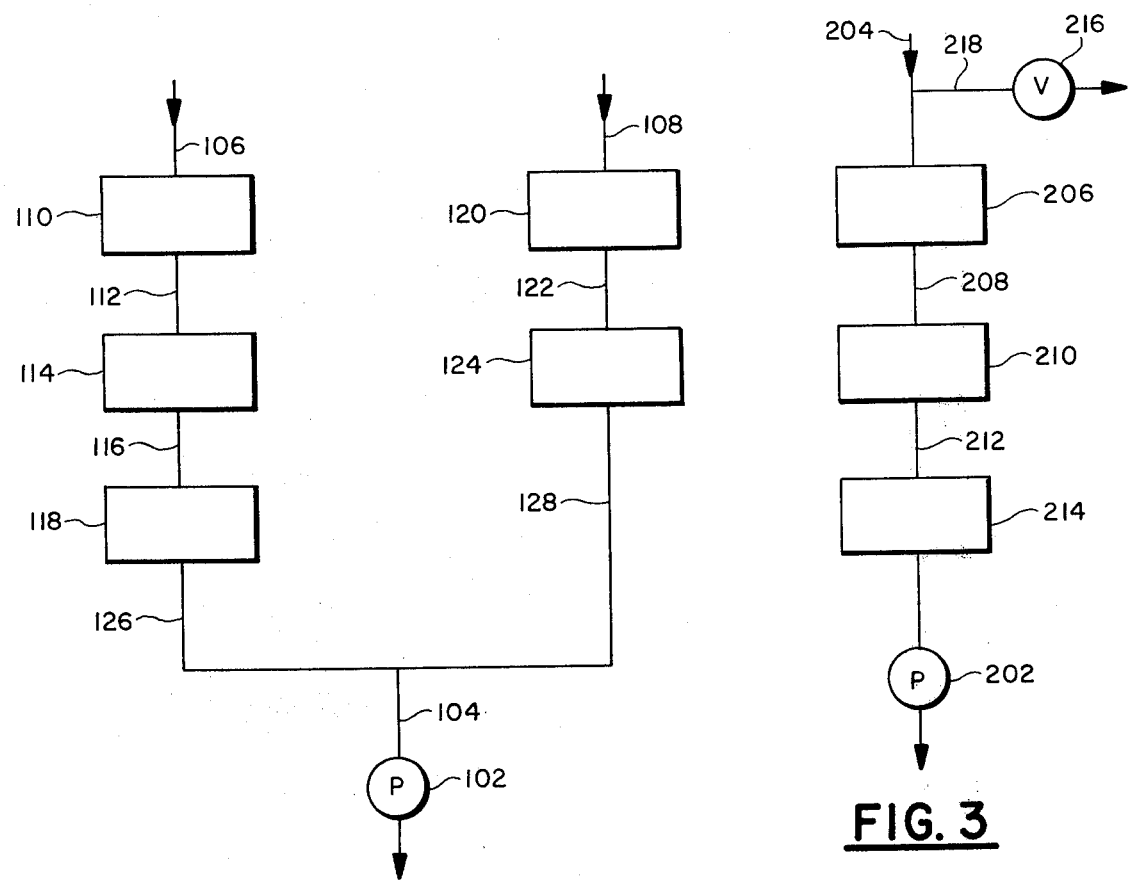
FIG. 2
FIG. 3

3,996,005

DETECTION AND MEASUREMENT OF $NO_2$ AND $O_3$

BACKGROUND OF THE INVENTION AND PRIOR ART

This invention relates to a method for the determination of $NO_2$ and ozone, to the reactions of $NO_2$ and ozone with solid alkali metal halides, and the reaction of $NO_2$ with various salts to produce NO.

In recent years, recognition of environmental limitations has led to widespread qualitative and quantitative studies and analysis of atmospheric pollutants, such as nitrogen dioxide and ozone. Numerous devices and techniques have been proposed over the years for detecting such pollutants. However, most of the prior art techniques and devices have sought to simply detect or make relatively gross measurements of the pollutants. Other prior art devices and techniques have permitted more refined quantitative measurements, but have required extensive time, skilled technicians, and equipment which was often elaborate, delicate, expensive and required considerable readjustment and maintenance. It has been found that the release of halogen permits measurement of pollutants at the parts-per-million level when employed with solid state gaseous halogen sensors, such as those disclosed in U.S. Pat. No. 3,764,269. However, the halogen release and measurement process has not been adapted to the measurement of combined $NO_2$ and $O_3$ because of the lack of a suitable reagent to produce halogen in the gaseous state at about ambient temperatures.

Further, it is known that when NO undergoes oxidation by $O_3$ to $NO_2$, there is a detectable light emission, the intensity of which is directly proportional to the NO so reacted. This reaction has been suggested as a means for detecting and measuring $NO_2$ in air by utilizing the thermal conversion of $NO_2$ to NO followed by re-conversion of NO to $NO_2$ by ozone and measurement of the light emission associated with the reaction. However, the thermal conversion of $NO_2$ to NO requires high temperatures in the order of 200° C and higher for completion and also converts $NH_3$ to NO.

SUMMARY OF THE INVENTION

It has now been found that both $NO_2$ and $O_3$ will react with solid alkali metal halides at ambient temperatures and above to release halogen gas which may be easily detected quantitatively to give a precise measurement of the combined concentration of nitrogen dioxide and ozone in the air sample; and that $NO_2$ may be reacted with certain metal halides to quantitatively convert the $NO_2$ to NO which can be accurately measured. The concentrations of $NO_2$ and $O_3$ may thus be determined by a combined measurement of the $O_3 + NO_2$ and a separate determination of the $NO_2$ concentration.

DETAILED DESCRIPTION

It is therefore an object of this invention to provide a method for the detection of $NO_2$.

Another object of the invention is the provision of a method for the detection of ozone.

A further object is the provision of a method for detecting the combined presence of $NO_2$ and ozone in air.

A still further object of this invention is to provide an apparatus for the production of a gaseous halogen from solid alkali halides when such halides are contacted with gases containing $NO_2$ and $O_3$.

Still another object of this invention is the provision of a method for the determination of $NO_2$ in air by conversion of the $NO_2$ to NO and subsequent determination of the NO concentration by the chemiluminescence method.

Still other objects of the invention will be apparent from the following detailed description of the invention and related claims.

Objects of this invention are accomplished by a process and apparatus for reacting $NO_2$ and $O_3$ with a solid alkali metal halide at ambient temperatures and above to produce a gaseous halogen and determining the relative amount of halogen produced as a measure of the $NO_2$ and $O_3$ reacted.

One aspect of the invention, more simply stated, is the reaction of $NO_2$ with a solid alkali metal halide to produce gaseous halogen where the alkali metal has an atomic weight of from 6 to 133, and the halogen has an atomic weight of from 19 to 127.

Another aspect of the invention is, again more simply stated, the reaction of ozone with a solid alkali metal halide as defined above to produce gaseous halogen. These reactions are preferably conducted in the presence of moisture.

An embodiment of the invention is an apparatus for the determination of $NO_2$ and $O_3$ in air which comprises means for supplying air to be analyzed, means for contacting said air with a solid alkali metal halide to release halogen in proportion to the concentration of $NO_2$ and $O_3$ therein and means for detecting and measuring the halogen thus produced.

Another embodiment of the present invention is a process and apparatus for determining the $NO_2$ and $O_3$ concentrations in air samples. This is accomplished by a system for taking two concurrent determinations of halogen concentration; one being taken on an air sample after reaction thereof with an alkali metal halide, and the other after processing the sample to remove ozone.

A still further embodiment of this invention comprises a method for the determination of $NO_2$ in air by converting the $NO_2$ to NO and measuring the quantity of NO by the chemiluminescence method.

This is accomplished by the reaction of the $NO_2$ with a suitable salt which brings about a quantitative conversion of the $NO_2$ to NO.

Among the salts which may be utilized in this aspect of the invention are $PbI_2$, $CuI$, $BiI_3$, $AuI$, $PdI_2$, $TlI$ and $ZnI_2$. However, a particularly preferred embodiment of this aspect of the invention is the conversion of $NO_2$ to NO by reaction thereof with lead iodide ($PbI_2$) because the reaction is essentially quantitative at temperatures well below 250° C.

BRIEF DESCRIPTION OF THE DRAWINGS

In the drawings accompanying this application;

FIG. 1 is a diagrammatic representation of a device embodying the present invention shown in cross section;

FIG. 2 is a diagrammatic representation of the process of another embodiment of the invention; and FIG. 3 is a schematic representation of still another embodiment of the invention.

DETAILED DESCRIPTION OF THE INVENTION

In that form of the present invention chosen for purpose of illustration in FIG. 1, a contaminant measuring device, indicated generally at 10, is shown comprising a cylindrical housing 12 which is open at each end 14 and 16. Within the housing 12 is mounted a halogen detecting device such as an electrolytic cell 18, by means of a spring 20 resting against one side of the cell 18 and the interior walls of the housing 12 at the open end 14 thereof, the cell 18 has an open Pt mesh electrode 22 pressed into a layer of solid silver halide 24, adjacent a silver electrode 26. The Pt mesh-silver halide layer is arranged to allow the passage of air through the housing 12 from the open side 16 to the outlet 14. The housing 12 has suitable means (not shown) to allow it to be opened for repair or replacement of the cell 20. From the electrodes 22 and 26 lead wires 28 and 30 project through the housing 12 to a suitable detection device or meter 32 to detect the output of the cell 18. Connected to the housing 12 at the end 16 is a second housing 34 communicating with both the cell containing housing 12 and an air inlet 36. Within the housing 34 is mounted a quantity of alkali metal halide reagent 38 in gas-permeable form. The capsule 38 may be formed by any suitable means, such as compressing the halide into a solid, yet porous, wafer or providing a pair of circular mesh discs which are secured together and are capable of retaining halide granules therebetween, yet permit the passage of gas.

In use, air is caused to flow through the inlet 36 through housing 34, by means of a pump or the like (not shown). In passing through the housing 34, the air will be forced to pass through reagent 38 and housing 12 containing the detector 18. If there is any ozone ($O_3$) or nitrogen dioxide ($NO_2$) present in the air, they will react with the halide salt yielding the corresponding halogen gas.

The halogen released by this reaction is then detected and measured by the cell 18 and the concentration of the halogen determined by the reading of the device 32. It has been found that this technique can accurately detect and measure the presence of $NO_2$ and $O_3$ to fractional parts per million in air. Moreover, this technique can be carried out at about ambient temperatures and is uneffected by relative humidity in the range of 30–80%. In practice, temperatures of from about 20° to about 50° C may be employed, but temperatures of from about 30° C to about 40° C are preferred because of the faster response times and faster reaction times.

To illustrate, without limitation, the practice of the present invention, a quantity of powdered NaI was placed in a glass tube and confined with glass wool. The tube was attached to a source of 50% wet air. Downstream from the tube containing the NaI was an electrolytic cell (Ag/AgI/Pt mesh) for detecting gaseous iodine. The NaI containing tube and the cell were temperature controlled at 35° C and the Pt and silver electrodes were connected to a voltage measuring device. Known quantities of $NO_2$ and $O_3$ were monitored into the air stream and the voltage output of the cell was observed. Data obtained are shown in Table 1 below:

TABLE 1

| $O_3$ PPM | $NO_2$ PPM | Voltage Observed |
|---|---|---|
| \multicolumn{3}{l}{VOLTAGES OBSERVED WITH KNOWN CONCENTRATIONS OF $NO_2$ AND $O_3$ IN AIR AFTER REACTION WITH NaI} | | |
| 0.05 | 0 | 0.560 |
| 0.109 | 0 | 0.568 |
| 0.218 | 0 | 0.578 |
| 0.435 | 0 | 0.587 |

TABLE 1-continued

| $O_3$ PPM | $NO_2$ PPM | Voltage Observed |
|---|---|---|
| \multicolumn{3}{l}{VOLTAGES OBSERVED WITH KNOWN CONCENTRATIONS OF $NO_2$ AND $O_3$ IN AIR AFTER REACTION WITH NaI} | | |
| 0 | 0.315 | 0.5885 |
| 0 | 0.225 | 0.584 |
| 0 | 0.120 | 0.575 |
| 0 | 0.110 | 0.575 |
| 0 | 0.072 | 0.569 |
| 0 | 0.043 | 0.563 |

The data indicate that the conversion of $O_3$ to iodine is about 42% complete based on the concentration of iodine measured by the cell, whereas the conversion of $NO_2$ is about 76% complete. Thus, a single determination of a contaminated air sample by the process of this invention illustrated in FIG. 1 gives a very close approximation of the total combined $O_3$ and $NO_2$ in the sample.

However to determine the amounts of $O_3$ and $NO_2$ individually in the sample, it is of course required that at least two measurements be made.

Among the alkali metal halide salts which may be employed in the capsule 38, in addition to sodium iodide, include sodium chloride, sodium bromide, potassium iodide, potassium bromide, potassium chloride. Likewise, the salts of cesium and rhubidium may be employed. In addition the salts of lithium may be employed, as may the alkali metal fluorides, but precautions must be taken to prevent side reactions. The preferred alkali metal salts are the iodides, of sodium and potassium.

It is to be noted that mixtures of the salts may be employed so long as the halide component remains the same, inasmuch as the silver halide component 24 of the cell 18 is always the same halide as the reagent in the housing 34.

To insure that there is sufficient moisture in the air being tested, it may be desirable to pass the air sample over (but not through) water prior to its passage through the tube 34.

It is further preferred that both the cell 18 and the tube 34 be at or near the same temperature. Thus they may be in a controlled temperature bath, or under the influence of thermostatically controlled heaters.

Turning now to the embodiment of the invention illustrated in FIG. 2, there is diagrammatically illustrated a pump 102 for forcing air to be analyzed through a set of parallel reactors and detectors. Air is drawn by the pump 102 through lines 126 and 128 and the intermediate equipment described below and intake lines 106 and 108. The air passing in line 106 is subjected to a scrubber 110 to remove $O_3$ and then passes, via line 112, to a reactor 114 containing an alkali metal halide, as illustrated at 34 and 36 of FIG. 1, to effect the production of halogen based on the concentration of $NO_2$ in the air. $O_3$ may be scrubbed from the sample by passing the air through cotton wool and by other methods well known in the art. The gas effluent from the reactor 114 passes, via line 116, to a halogen detector cell 118 (as illustrated in detail at 12 and 18 of FIG. 1) to measure the halogen concentration of the air resulting from the reaction of $NO_2$ and alkali metal halide at 114. Simultaneously, the air passing through line 108 enters a second reactor 120 containing alkali metal halide in gas permeable form. In the reactor 120, as in the embodiment of the invention illustrated in FIG. 1, both $NO_2$ and $O_3$ react to release halogen from the alkali metal halide. The air, now containing halogen, passes to the detector 124 through line 122. The detector 124 may be the same type cell and housing illustrated above in FIG. 1 and will indicate the halogen concentration of the air effluent from the reactor 120, giving an indication of the combined concentration of $NO_2$ and $O_3$ in the air entering the apparatus through line 108. After detection of the halogen in detectors 118 and 124, reaction products are exhausted from the device through exhaust line 104 and pump 102 after passing through lines 126 and 128.

In order to obtain an indication of the individual concentrations of $NO_2$ and $O_3$ by use of the methods of this invention, it is desirable to experimentally develop a series of curves of the voltage generated with varying amounts of ozone while holding the $NO_2$ concentration constant. For example, by measuring the voltage generated at known $NO_2$ concentrations of about 0.03, 0.05, 0.07, 0.10, 0.20, 0.40 and 0.60 PPM and, at each $NO_2$ level, taking measurements of varying $O_3$ concentrations over about the same concentration, a family of curves is generated which will enable one skilled in the art to determine the $O_3$ concentration by interpolation between these curves once the $NO_2$ concentration has been determined. The $NO_2$ determination may be taken as illustrated above in FIGS. 1 and 2, or may be determined as described below. The combined $NO_2$—$O_3$ determination is by the method and apparatus of FIG. 1.

In a preferred embodiment of the invention, schematically illustrated in FIG. 3, the $NO_2$ is determined by the quantitative conversion thereof to NO and subsequent measurement of the NO by the chemiluminescence method. Thus, as illustrated in FIG. 3, air is drawn by pump 202 through line 204 into $O_3$ scrubber 206 where any $O_3$ present is removed. The ozone free air then passes through line 208 to the reactor 210 where any $NO_2$ present reacts essentially quantitatively with $PbI_2$ contained in a gas permeable capsule as described in connection with FIG. 1 above, to form NO. Effluent gases from the reactor 210 pass to the chemiluminescence reactor-detector 214 through line 212.

In the reactor-detector 214 NO resulting from the $PbI_2$— $NO_2$ reaction in reactor 210 is first reacted with $O_3$ to again form $NO_2$. About 10 percent of the $NO_2$ produced in this reaction is electronically excited, and its transition to the unexcited state is accompanied by a detectable light emission at low pressure, as has been described, for example by SIGSBY, et al, Environmental Science and Technology, Volume 7, Number 1, page 51–54 (January 1973).

Thus, the reactor-detector shown schematically at 214 includes the means required to provide $O_3$ to the sample, reduce the pressure, and measure the light emission of the $NO_2$ produced.

There are commercially available pieces of equipment capable of measuring the light emission resulting from the $O_3$ + NO reaction.

Alternatively, the $NO_2$ concentration in the line 208 may be measured by the halogen detection cell described above, inasmuch as the reaction of $NO_2$ with $PbI_2$ quantitatively releases iodine while converting the $NO_2$ to NO.

As further shown in FIG. 3, the device may be fitted with a valve 216 to permit the draw off of an air sample through line 218. This sample may be fed to the apparatus of FIG. 1 for the simultaneous determination of the combined $O_3$ and $NO_2$ in input air supply.

To illustrate the results obtained in determining the extent of $NO_2$ contamination in air, an experimental apparatus including the reactor 210 and reactor-detector 214 of FIG. 3 was employed. The experimental equipment also included a source of $NO_2$ and $O_3$ free air and a source of $NO_2$. The experimental equipment was arranged so that controlled amounts of wet air and $NO_2$ were mixed together and the concentration of $NO_2$ measured by thermally converting the $NO_2$ to NO, then reacting the NO to $NO_2$ and determining the $NO_2$ concentration by the chemiluminescence method.

The conversion to NO, reconversion to $NO_2$ and light detection were accomplished in a Bendix Chemiluminescent Nitrogen Oxide detector. Using the same flow rates of air and $NO_2$, the mixture was then subjected to the process illustrated in FIG. 3 above; that is, subjected to reaction with $PbI_2$ to convert the $NO_2$ to NO followed by reaction of the resulting NO with $O_3$ and measurement of the chemiluminescence of the resulting $NO_2$.

Using the above procedure, dry air at 60 ml/min nd wet air (61.9 ml/min), yielding a mixture at 49.5% relative humidity, was caused to flow through the apparatus and was mixed with $NO_2$ to give a mixture calculated to contain 0.99 parts per million $NO_2$ by volume. However, analysis of this mixture by the thermal conversion of $NO_2$ to NO and reconversion to $NO_2$ by $O_3$ reaction, followed by measurement of the chemiluminescence of the $NO_2$ thus produced indicated 1.14 parts per million $NO_2$. The same gas stream was then reacted with $PbI_2$ at varying temperatures, using 3.2 grams of $PbI_2$ in the reactor; the NO produced reacted with $O_3$ and the chemiluminescence determined. The results are summarized in Table 2 below.

TABLE 2

| CHEMILUMINESCENCE MEASUREMENT OF NO PRODUCED FROM $NO_2$ IN AIR BY REACTION WITH $PbI_2$ | |
|---|---|
| Temperature ° C | $NO_2$ PPM |
| 60 | 0.84 |
| 80 | 0.915 |
| 100 | 0.98 |
| 110 | 1.00 |
| 120 | 1.04 |
| 125 | 1.05 |
| 130 | 1.06 |

In other, similar determinations it was found that a near quantitative determination of the $NO_2$ in the parts per million range down to about 0.1 PPM in the original gas stream can be made by employing flow rates of up to about 250 ml/min at temperatures from about 100° to 250° C using 0.45 grams or more of $PbI_2$. Temperatures in the range of from about 110° C to about 190° C are preferred because the reaction is rapid and essentially quantitative in that range.

I claim:

1. A method for the determination of $NO_2$ in air which comprises reacting air containing $NO_2$ with solid $PbI_2$, $CuI$, $BiI_3$, $AuI$, $PdI_2$, $TlI$ or $ZnI_2$ to effect an essentially quantitative conversion of said $NO_2$ to NO, and subsequently determining the quantity of NO produced.

2. A method for the determination of $NO_2$ in air which comprises reacting air containing $NO_2$ with solid $PbI_2$ to effect an essentially quantitative conversion of said $NO_2$ to NO, and subsequently determining the quantity of NO produced.

3. A method for determining the concentrations of $O_3$ and $NO_2$ in air which comprises separating an air stream to be analyzed into two separate increments; contacting one of said increments with a solid alkali metal halide to convert any $O_3$ and $NO_2$ present to gaseous halogen and determining the halogen concentration thus produced; and contacting the other of said increments with solid $PbI_2$ to convert any $NO_2$ present to NO and determining the concentration of NO produced as a measure of the $NO_2$; and determining the $O_3$ concentration by differences.

* * * * *